United States Patent [19]

Harandi et al.

[11] Patent Number: 5,059,744
[45] Date of Patent: Oct. 22, 1991

[54] REACTOR AND RECOVERY SYSTEM FOR UPGRADING LOWER OLEFINS

[75] Inventors: Moshen N. Harandi, Lawrenceville; Hartley Owen, Belle Mead, both of N.J.

[73] Assignee: Mobil Oil Corporation, Fairfax, Va.

[21] Appl. No.: 414,863

[22] Filed: Sep. 29, 1989

Related U.S. Application Data

[63] Continuation-in-part of Ser. No. 163,498, Mar. 3, 1988, Pat. No. 4,879,428.

[51] Int. Cl.$^5$ .............................................. C07C 2/12
[52] U.S. Cl. .................................... 585/921; 585/314; 585/315; 585/316; 585/322; 585/415; 585/533
[58] Field of Search ............... 585/921, 920, 533, 314, 585/315, 316, 322, 329, 415

[56] References Cited

U.S. PATENT DOCUMENTS

| | | | |
|---|---|---|---|
| 4,211,640 | 7/1980 | Garwood et al. | 208/255 |
| 4,456,779 | 9/1984 | Owen et al. | 585/415 |
| 4,504,693 | 3/1985 | Tabak et al. | 585/520 |
| 4,544,788 | 10/1985 | Daviduk et al. | 585/501 |
| 4,544,792 | 10/1985 | Smith et al. | 585/533 |
| 4,547,612 | 10/1985 | Tabak | 585/533 |
| 4,720,600 | 1/1988 | Beech, Jr. et al. | 585/330 |
| 4,788,366 | 11/1988 | Harandi et al. | 585/314 |
| 4,879,428 | 11/1989 | Harandi | 585/533 |

*Primary Examiner*—Asok Pal
*Attorney, Agent, or Firm*—A. J. McKillop; C. J. Speciale; L. G. Wise

[57] ABSTRACT

An improved olefin upgrading technique and fixed-bed reactor system has been developed for increasing production of premium heavy hydrocarbons, such as distillate fuel, from lower olefinic feedstock. During recovery and recycle of intermediate range hydrocarbons products, a technique has been found for withdrawing a fraction rich in $C_5$–$C_9$ gasoline range olefinic hydrocarbons from the oligomerization reactor effluent stream. By separating the reaction effluent in a multi-stage distillation system, fractionation feed can be separated into a heavier bottoms stream rich in $C_{10}+$ hydrocarbons and a light hydrocarbon overhead, while withdrawing a liquid stream as an overflash fractionation stream rich in intermediate hydrocarbons. The overflash stream is combined to form a portion of the recycle stream to the reactor, thereby providing a more efficient and lower cost recovery process.

9 Claims, 3 Drawing Sheets

REACTOR AND RECOVERY SYSTEM FOR UPGRADING LOWER OLEFINS

REFERENCE TO CO-PENDING APPLICATION

This application is a continuation in part of co-pending U.S. patent application Ser. No. 07/163,498 filed Mar. 3, 1988, incorporated herein by reference, now U.S. Pat. No. 4,879,428.

FIELD OF INVENTION

This invention relates to a continuous reactor system with improved product recovery for increasing production of distillate range hydrocarbon fuels. In particular it provides a system for operating an olefins upgrading plant wherein acid oligomerization catalyst, such as medium pore zeolite, is employed for converting olefinic feedstocks containing alkenes at elevated temperature and pressure.

BACKGROUND OF THE INVENTION

Conversion of lower olefins to gasoline and/or distillate products is disclosed in U.S. Pat. Nos. 3,960,978 and 4,021,502 (Givens, Plank and Rosinski) wherein gaseous olefins in the range of ethylene to pentene, either alone or in admixture with paraffins, are converted into an olefinic gasoline blending stock by contacting the olefins with a catalyst bed comprising ZSM-M zeolite.

In a related manner, U.S. Pat. Nos. 4,150,062, 4,211,640 and 4,227,992 (Garwood, et al) disclose fixed-bed catalytic processes for converting olefins to gasoline and/or distillate components. In U.S. Pat. No. 4,456,779 (Owen, et al) and U.S. Pat. No. 4,443,185 (Tabak), incorporated herein by reference, operating conditions are disclosed for an olefin upgrading process for selective conversion of $C_3+$ olefins to mainly aliphatic hydrocarbons.

Typically, the process recycles gas or liquid hydrocarbons from a high-temperature, high-pressure separator downstream of the catalyst bed back into the reaction zone where additional olefins are converted to gasoline and distillate products. If the reaction of the olefins in converting them to distillate and gasoline is allowed to progress adiabatically in the catalyst zone without any measures taken to prevent the accumulation of heat, the reaction becomes so exothermically accelerated as to result in high temperatures and the production of undesired products. The amount of recycle and the composition of the gas are critical to precise control of the reaction exotherm. Accordingly, in the conventional process, extra separation steps are included to separate a fraction from the reaction effluent which has the appropriate composition to function as a recycle liquid to the reaction zone. These additional separation steps represent a significant cost to the overall process.

In the process for catalytic conversion of olefins to heavier hydrocarbons by catalytic oligomerization using a medium pore shape selective acid crystalline zeolite, such as ZSM-5 catalyst, process conditions can be varied to favor the formation of either gasoline or distillate range products. At moderate temperature and relatively high pressure, the conversion conditions favor aliphatic distillate range product having a normal boiling point of at least 165° C. (330° F.). Lower olefinic feedstocks containing $C_2$-$C_8$ alkenes may be converted; however, the distillate mode conditions do not convert a major fraction of ethylene. One source of olefinic feedstocks of interest for conversion to heavier fuel products is the intermediate olefin-rich naphtha or light oil obtained as a liquid product from Fischer-Tropsch conversion of synthesis gas.

A typical feedstock consists essentially of $C_3$-$C_6$ mono-olefins with a minor amount of coproduced oxygenate from Fischer-Tropsch synthesis. These feedstocks are suitable for upgrading to more valuable heavier hydrocarbon; however, the organic oxygenated content may cause catalyst aging due to formation of coke during the conversion process. Typically, hydrogen is co-fed to the a fixed-bed catalytic reactor to reduce coking of the catalyst.

During the course of a single catalyst cycle, fixed-bed reactor inlet temperature must be raised to maintain the desired conversion of olefins to gasoline and/or distillate, and to maintain desired product liquid quality. Beyond a certain temperature, these objectives cannot be met and the catalyst must be regenerated. It is desirable to minimize the frequency of regeneration by decreasing the temperature aging rate. This reduces the inconvenience and cost of frequent regeneration, and may also extend the ultimate life of the catalyst, which experiences permanent activity loss over the course of many regenerations.

It is a main object of this invention to provide a continuous reactor system devised for upgrading olefins to a valuable heavy distillate fuel product.

It is a further object of this invention to provide an improvement to the downstream product recovery apparatus for the separation of a liquid recycle dilvent stream to the oligomerization reactor or conversion zone leading to a simplified and lower cost conversion process.

SUMMARY OF THE INVENTION

It has been found that separation of the requisite liquid recycle stream to the conversion or reaction zone of the process for upgrading of lower olefins to higher hydrocarbons rich in $C_{10}+$ distillate product is improved by providing two low-temperature separators A typical feedstock consists essentially of $C_3$-$C_6$ mono-olefins with a minor amount of coproduced oxygenate from Fischer-Tropsch synthesis. These feedstocks are suitable for upgrading to more valuable heavier hydrocarbon; however, the organic oxygenated content may cause catalyst aging due to formation of coke during the conversion process. Typically, hydrogen is co-fed to the a fixed-bed catalytic reactor to reduce coking of the catalyst.

During the course of a single catalyst cycle, fixed-bed reactor inlet temperature must be raised to maintain the desired conversion of olefins to gasoline and/or distillate, and to maintain desired product liquid quality. Beyond a certain temperature, these objectives cannot be met and the catalyst must be regenerated. It is desirable to minimize the frequency of regeneration by decreasing the temperature aging rate. This reduces the inconvenience and cost of frequent regeneration, and may also extend the ultimate life of the catalyst, which experiences permanent activity loss over the course of many regenerations.

It is a main object of this invention to provide a continuous reactor system devised for upgrading olefins to a valuable heavy distillate fuel product.

It is a further object of this invention to provide an improvement to the downstream product recovery apparatus for the separation of a liquid recycle diluent stream to the oligomerization reactor or conversion zone leading to a simplified and lower cost conversion process.

SUMMARY OF THE INVENTION

It has been found that separation of the requisite liquid recycle stream to the conversion or reaction zone of the process for upgrading of lower olefins to higher hydrocarbons rich in $C_{10}+$ distillate product is improved by providing two low-temperature separators

THE DRAWINGS

DESCRIPTION OF THE PREFERRED EMBODIMENTS

Figure 1:
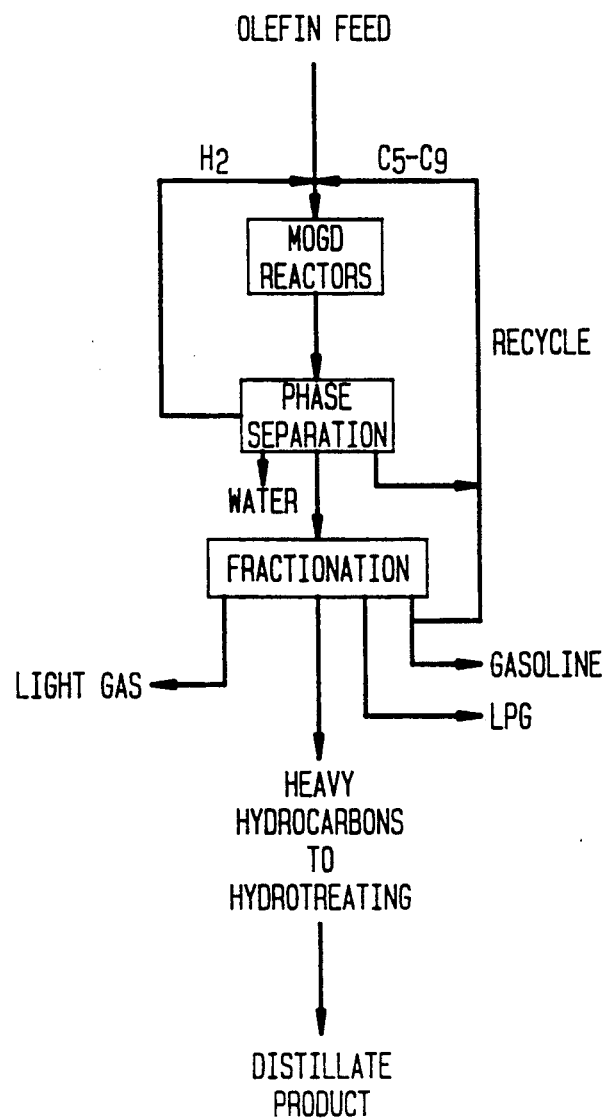
FIG. 1 is process flow sheet showing the major unit operations and process streams.

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such Al, Ga, or Fe, within the zeolytic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recongized by its X-ray diffraction pattern, which is described in U.S. Pat. No. 3,702,866 (Argauer, et al.), incorporated by reference.

The oligomerization catalysts preferred for use herein include the crystalline aluminosilicate zeolites having a silica to alumina ratio of at least 12, a constraint index of about 1 to 12 and acid cracking activity greater than 120, preferably about 160 to 200. Representative of the ZSM-5 type zeolites are ZSM-5, ZSM-11, ZSM-12, ZSM-23, ZSM-35, and ZSM-48. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,842 for ZSM-23 and U.S. Pat. No. 4,016,245 for ZSM-35. The disclosures of these patents are incorporated herein by reference. A suitable shape selective medium pore catalyst for fixed bed is HZSM-5 zeolite with alumina binder in the form of cylindrical extrudates of about 1-5 mm. Other pentasil catalysts which may be used in one or more reactor stages include a variety of medium pore siliceous materials such as borosilicates, ferrosilicates, and/or aluminosilicates disclosed in U.S. Pat. Nos. 4,414,423, 4,417,086, 4,417,088 incorporated herein by reference.

The zeolite catalyzes a number of known reactions in addition to the oligomerization-interpolymerization reactions which are favored in producing the $C_{10}-C_{20}$ or higher molecular weight aliphatic materials useful as distillate fuel, etc. At higher temperatures, acid cracking, ends to diminish product yield. Bronsted acid sites are provided by strong aluminosilicates and it is preferred to maintain a high effective alpha-value, although certain metal cation-exchanged zeolites may be useful.

Catalyst aging can be caused by accumulation of very heavy product and/or process coke. It is known that relatively pure olefin feedstocks cause only minor deposition of non-strippable coke. The heavy hydrocarbonaceous deposits accumulated by non-oxygenated hydrocarbon can be stripped by high temperature gases. Harder process coke which results from dehydration and conversion reactions involving alcohols, ketones, aldehydes, etc., cannot be adequately rejuvenated or regenerated by stripping alone, and oxidative reactivation is required to restore the catalyst to substantially full activity.

The presence of water in the reaction zone is known to cause steaming of the catalyst with reduced catalyst activity. Water may be present from oxygenates or as part of the recycle stream to the reaction zone. The reduction of water content in the recycle stream as in the present invention has a salutary effect on catalyst life. In the present invention, recycle stream water content is significatly reduced by about 20%, compared to prior art processes.

The flowsheet diagram of FIG. 1 shows the relationship of the inventive process operations and fractionation unit operations, depicting the recycle and further conversion of the $C_5-C_9$ rich olefinic intermediate. Heavy hydrocarbons may be recovered by fractionation and sent to a conventional hydrotreating unit for product finishing. Feedstock may be from olefins produced via syngas by Fischer-Tropsch chemistry or provided as a light olefin stream, such as $C_3-C_6$ olefins.

The present invention provides a continuous economic process for converting lower olefins to heavier hydrocarbons. It is an object of the present invention to separate olefinic gasoline range hydrocarbons from reactor effluent in an efficient manner to provide a recycle stream rich in $C_5$ to $C_9$ hydrocarbons and having only minor amounts of $C_4$-compounds. compounds. The gasoline recycle stream is obtained by novel phase separation and distillation overflash techniques, wherein the reactor effluent stream is cooled to condense liquid hydrocarbons, especially $C_{10}+$ distillate materials, which are recovered in a liquid stream. These aspects are shown in greater detail in FIG. 2 and in the following description.

GENERAL PROCESS DESCRIPTION

Figure 2:
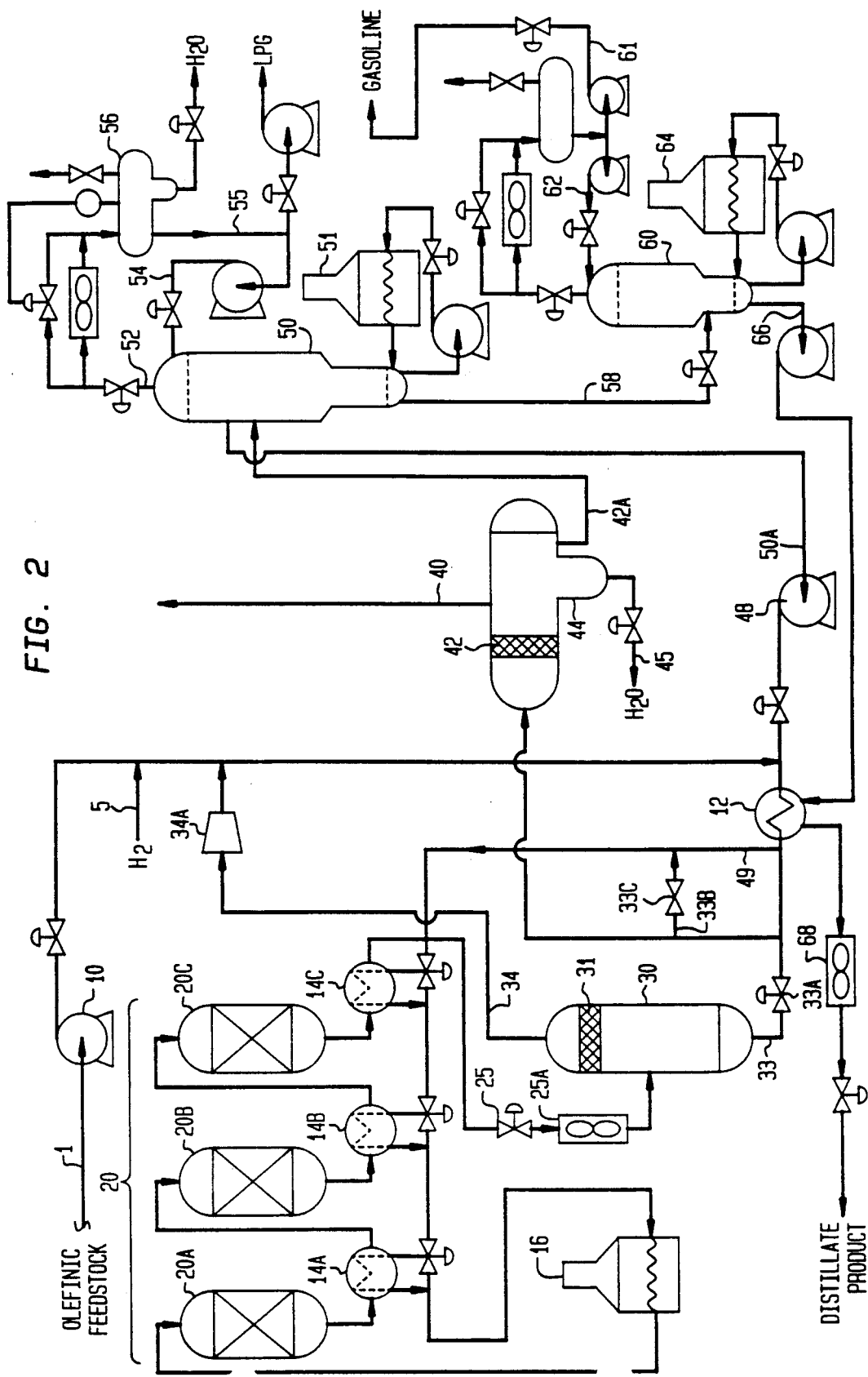
FIG. 2 is a schematic representation of a fixed bed reactor system and product separation system.

Referring to FIG. 2 the olefinic feedstock supply 1 is normally liquid and can be brought to process pressure by means of pump 10. Pressurized hydrogen gas is supplied via conduit 5 and combined with feedstock, which is preheated by passing through a heat exchange means 12, and reactant effluent exchangers 14C, B, A, and furnace 16 prior to entering the catalytic reactor system 20.

A typical distillate mode first stage reactor system 20 is shown. A multi-reactor system is employed with inter-zone cooling, whereby the reaction exotherm can be carefully controlled to prevent excessive temperature above the normal moderate range of about 230° C. to 325° C. (450°-620° F.). While process pressure may be maintained over a wide range, usually from about 2800 to over 10,000 kPa (400-1500 psia), the preferred pressure is about 4000 to 7000 kPa (600 to 1000 psia). The feedstock is heated to reaction temperature and carried sequentially through a series of zeolite beds 20A, B, C wherein at least a portion of the olefin content is converted to heavier distillate constituents. Advantageously, the maximum temperature differential across only one reactor is about 30° C. (50° F.) and the space velocity (LHSV based on olefin feed) is about 0.5 to 1.5. The heat exchangers 14A and 14B provide inter-reactor cooling and 14C reduces the effluent to flashing temperature. Control valve 25, and heat exchanger 25A operatively connected between the reactor section 20 and phase separator unit 30 provides means for reducing the process pressure and temperature to about 38° C. and 4250 kPa thereby flashing volatile components of the effluent stream, such as hydrogen and unreacted lighter hydrocarbons. A demister pad 31 prevents substantial liquid entrainment and a major amount of the overhead vapor is withdrawn through conduits 34 compressed in compressor 34A and recycled through heat exchanger 12 to the reaction zone.

Liquid hydrocarbons rich in distillate are recovered from separator 30 and a portion passed to separtor tank 42 through control valve 33A. That portion not passed to separator 42 is recycled to the reaction zone through conduit 33B, control valve 33C and conduit 49. In separator 42, the liquid hydrocarbon is separated at a temperature of about 50° to 25° C., preferably about 40° C. (104° F.), and a pressure of about 800 to 2000 kPa, preferably about 1330 kPa (190 psig).

Separator tank 42 has an overhead gas conduit 40 for removing a hydrogen-rich stream and separate a water phase, which is withdrawn from the system through boot 44 and outlet 45.

Condensed hydrocarbons from separator 42 are passed 42A to fractionating tower 50 at a lower stage therein where the heavy liquid contacts rising vapor from reboiler section 51 to vaporize dissolved lighter hydrocarbons, especially $C_4$-hydrocarbons present in the feedstock or generated during conversion. The debutanizer overhead stream 52 may be cooled to produce reflux 54 and recovered as LPG byproduct through conduit 55 from accumulator 56.

From distillation tower 50 an overflash liquid stream rich in $C_5$-$C_9$ hydrocarbons is withdrawn, preferably from an upper stage thereof. The overflash liquid stream is combined with the recycle liquid stream to the reaction zone through conduit 50A pump 48, heat exchanger 12 and conduit 49.

Light hydrocarbons and byproduct water are withdrawn with the tower overhead stream 52 and heavier hydrocarbons containing gasoline and/or distillate range hydrocarbons are sent along with the distillation bottoms stream 58 to product splitter 60 where the heavier hydrocarbons are fractionated to provide a condensed gasoline product 61 and condensed reflux 62. Light gas from separator 56 is rich in $H_2$ nad $C_2$-components. This off-gas may be used as fuel gas, or the hydrogen may be recovered by a hydrogen purification unit (not shown) and recycled under pressure, as described above. Splitter tower 60 has a furnace fired reboiler section 64 and the refined heavy distillate product is recovered through conduit 66, and cooled by incoming feedstock in exchanger 12 and in cooler 68. Advantageously, the distillate-rich liquid phase is fractionated to provide a major product stream consisting essentially of 154° C. plus aliphatic hydrocarbons comprising a major amount of $C_{10}$-$C_{20}$ aliphatic hydrocarbons. This product may then be hydrotreated to provide a heavy distillate product.

There are several advantages to the process design. Usually the intermediate liquid recycle consists essentially of $C_5$+ hydrocarbons, with minor amounts of $C_4$-components. This recycle material has a relatively high heat capacity and provides a good heat sink without diminishing feedstock olefin partial pressure and thereby maintaining a high olefin partial pressure at reactor inlet. The distillate product quality is readily altered by changing the average molecular weight of recycled olefins. By increasing temperature of the overflash recycle stream, a heavier distillate product with regulated viscosity is obtained, and the recycled portion is further upgraded to heavier product by further reaction. The liquid recycle is economically repressurized by. The debutanizer is operable at about 1000 kPa (150 psi) to condense all overhead without refrigeration, thus providing energy efficiency in obtaining the LPG byproduct. The product splitter tower can be operated at atmospheric pressure, thus holding the bottoms temperature to less than 273° C. (525° F.) to provide raw distillate product stability.

Figure 3:
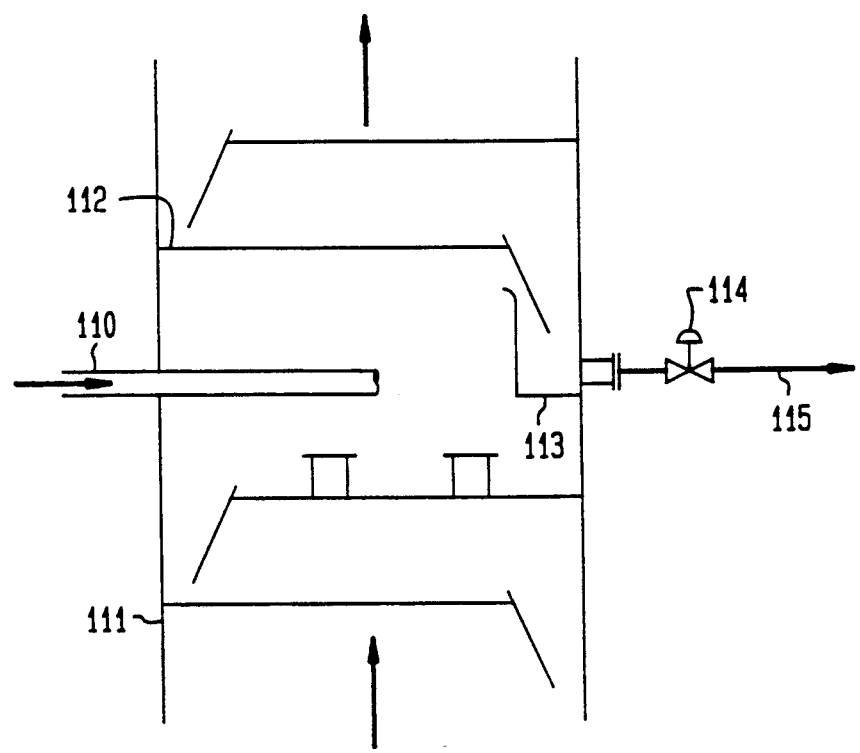
FIG. 3 is a diagram of the distillation tower overflash draw as used in the present invention.

An important feature of the present invention is the utilization of an overflash draw from the first distillation tower to provide the balance of the recycle stream to the conversion zone in combination with a portion of the liquid stream from the first low temperature separator. In the present invention, unstabilized gasoline which condenses on the tray above the feed to the distillation tower is withdrawn as the light gasoline recycle source to the conversion zone. Referring to FIG. 3, a sketch of the overflash draw is presented. A mixed phase feed enters through conduit 110 into the tower 111. Liquid from first tray 112 above the feed conduit spills into draw box 113 from which it is withdrawn through valve 114 and conduit 115. The use of overflash draw is generally known to those skilled in the art and is further described in U.S. Pat. No. 4,698,138 to Silvey, incorporated herein by reference as to the practice of recovery of overflash liquids.

In Table A, the composition of the overflash stream is shown with feed composition to the distillation tower and total hydrocarbons recycle.

TABLE A

| Recycle Distillation Overflash As Liquid Recycle | | | |
|---|---|---|---|
| | Distillation Overflash* | Distillation Feed | Total Hydrocarbons Recycle |
| $C_2$− | 0.1 | 0.9 | 0.7 |
| LPG | 21.1 | 19.1 | 17.0 |
| $C_5$+ Gasoline | 77.7 | 57.4 | 65.9 |
| Distillate | 1.1 | 22.6 | 16.3 |
| Total Flow Rate, Moles/Hr. | 512 | 2580 | 3210 |

*Assuming the overflash stream temperature of 114° C. (238° F.) and pressure of 910 kPa.

In prior art processes for the conversion of olefins to higher hydrocarbons with zeolite catalyst the product recovery section is complicated in that two low temperature and two high temperature separators are required to meet the specific needs of liquid recycle quality and hydrogen requirements. The recovered $H_2$ from the recovery system should be cooled before being compressed and recycled. The above constraint requires addition of low temperature separators after each high temperature separator located in the $H_2$ recovery section and/or utilized for providing part of the reactor liquid recycle. This results in a 4 separator design which includes 2 high temperature separators with two sets of overhead coolers and two low temperature separators to recover $H_2$ from the reactor effluent at low temperatures.

In the present invention high temperature separators are eliminated. In the design the reactor effluent is cooled to 40° C. (100° F.) and flashed at high pressure. Then the liquid from the described separator is throttled and flashed at a medium pressure level. The two low temperature flash system eliminates the need for the additional coolers and separators. In addition, $H_2$ is recovered at low temperatures, high purity and excellent percent recovery.

The advantages of the design of the present invention using two low temperature separators plus recycling liquid from the first separator combined with an overflash stream from the distillation tower are: elimination of a first stage compressor; lowering of second stage compressor power requirements; elimination of two separators and associated equipment; elimination jof four coolers; reduction of distillation tower recycle pump size; 800% increase in LPG recovery. The design eliminates asubstantial amount of equipment and reduces operating complexity.

In the following Tables, the prior art design (A) is compared to the design of the present invention (B).

TABLE 1

| INDIVIDUAL LIQUID RECYCLE STREAMS, MLBS/HR | | |
| --- | --- | --- |
| Recycle Source | A | B |
| Separator Systems | 315 | 277 |
| Distillation Side Draw | 0 | 49 |
| G/D Splitter Side Draw | 31 | 45 |
| G/D Splitter Overhead | 26 | 0 |
| Liquid Total | 372 | 371 |

Table 1 shows that the recycle rate is the same for designs, with less recycle taken from the separator system in the present invention.

TABLE 2

| LIQUID RECYCLE QUALITY* | | | |
| --- | --- | --- | --- |
| Wt. % | Specification | A | B |
| C4- | 5–9 | 8.9 | 8.2 |
| C5 -310 | 36–45 | 36.8 | 37.9 |
| 310–450 | 28–45 | 28.5 | 28.3 |
| 450+ | 5–27 | 25.8 | 26.3 |

*Recycle Quality was optimized for both cases to minimize debutanizer & G/D splitter loadings. The recycle quality in both cases can be controlled with sufficient flexibility by adjusting individual recycle streams.

Table 2 shows that liquid recycle quality is essentially the same for the two systems.

TABLE 3

| OVERALL MATERIAL BALANCE, M LBS/HR | | |
| --- | --- | --- |
| | A | B |
| Fresh Feed | 220.5 | 220.5 |
| $H_2$ Makeup | 0.1 | 0.1 |
| $H_2$ Purge | (0.3) | (0.4) |
| Off-Gas | (7.5) | (6.6) |
| Wild LPG | (13.3) | (14.0) |
| Gasoline | (70.2) | (70.2) |
| Distillate | (129.4) | (129.4) |

Table 3 shows that the overall material balance for the two systems is essentially identical.

TABLE 4

| MAJOR EQUIPMENT SIZE COMPARISON | | | |
| --- | --- | --- | --- |
| Hydrogen Recycle, Low Pressure compressor, GHP | 141 | 52 | 63% |
| Hydrogen Recycle, | 241 | 199 | 17% |

TABLE 4-continued

| MAJOR EQUIPMENT SIZE COMPARISON | | | |
| --- | --- | --- | --- |
| High Pressure compressor, GHP G/D Splitter: | | | |
| Diameter, Ft. | 12.5 | 11 | 12% |
| Height, Ft. | 100 | 100 | 0% |
| Reboiler, MMBTU/HR | 46 | 35 | 24% |
| Condenser, MMBTU/HR | 46 | 46 | 0% |
| Debutanizer | | | |
| Diameter, Ft. | 7 | 7 | 0 |
| Height, Ft. | 100 | 100 | 0 |
| Reboiler, MMBTU/HR | 19 | 22 | (16%) |
| Condenser, MMBTU/HR | 20 | 24 | (20%) |

As shown in Table 4, there are substantial advantages in major equipment sizing for the design of the present invention.

Feedstock may be any synthetic or petroleum derived olefins stream containing $C_3$–$C_6$ olefins.

Various modifications can be made to the system, especially in the choice of equipment and non-critical processing steps. While the invention has been described by specific examples, there is no intent to limit the inventive concept as set forth in the following claims.

We claim:

1. A continuous reactor system having improved product recovery for upgrading lower olefinic feedstock to higher hydrocarbons rich in $C_{10}+$ distillate product, comprising:

reactor means for contacting said feedstock with a fixed-bed solid acid oligomerization acid zeolite catalyst under oligomerization reaction conditions at elevated temperature and pressure in the presence of hydrogen to convert olefins to heavier hydrocarbons, thereby providing a hot reaction effluent stream containing light gas, $C_5$–$C_9$ intermediate hydrocarbon and $C_{10}+$ distillate hydrocarbons;

heat exchange means for cooling said effluent stream to recover a liquid stream comprising $C_5+$ hydrocarbons;

means for recycling a first portion of said liquid stream to said reacotor means;

means for fractionating a second portion of said liquid stream in a multistage distillation tower to recover a distillate hydrocarbon product stream comprising $C_{10}+$ hydrocarbons and a light overhead gas stream;

means for recovering an overflash liquid stream rich in $C_5$–$C_9$ intermediate hydrocarbons from an upper stage of said distillation tower;

means for recycling said overflash liquid stream to said reactor means in combination with said first portion of said liquid stream.

2. The reactor system of claim 1 wherein the acid catalyst comprises shape selective medium pore metallosilicate zeolite and is essentially free of hydrogenation components.

3. The reactor system of claim 2 wherein said acid metallosilicate zeolite catalyst has a constraing index of about 1 to 12.

4. The system of claim 1 including means for combining the feedstock with the olefinic recycle stream in a ratio of at least about 2 moles of recycle per mole of feedstock olefin.

5. A product separation system for the improved separation of hydrocarbon and hydrogen recycle streams to an olefins to gasoline and distillate conversion zone, comprising in combination:

first low temperature separator means operatively connected to said conversion zone for separating gaseous hydrogen recycle stream and first liquid hydrocarbon stream at essentially conversion zone pressure;

second low temperature separator means operatively connected to said first separator for further separation at reduced pressure of a portion of first liquid hydrocarbon stream into gaseous and liquid components;

pressure reducing means operatively connected to and in communication with said first and second separators for pressure reducing a portion of said first liquid hydrocarbon stream;

fractionation means operatively connected to said second low temperature separator means for fractionation of said liquid component therefrom;

conduit means comprising control valve and conduit operatively connected to a mid-portion of said fractionation means for withdrawing an overflash stream for recycling to said conversion zone in combination with a second portion of said first separator liquid hydrocarbon stream.

6. A continuous reactor system for the conversion of lower olefins feedstock to gasoline and distillate range products, comprising:

contacting catalytic reactor means for light olefinic feedstock and a diluent stream with oligomerization catalyst in a fixed-bed conversion zone under oligomerization conditions at elevated temperature and pressure whereby a conversion zone effluent stream rich in $C_5+$ hydrocarbons is produced;

means for cooling and passing said effluent stream;

first low-temperature separator means operatively connected to receive said effluent stream at essentially conversion zone pressure for recovering gaseous stream comprising hydrogen and light gases and a liquid stream comprising $C^5+$ hydrocarbons;

means for compressing and recycling said gaseous stream to said conversion zone;

means for passing a first portion of said first separator liquid stream to second low-temperature separator at reduced pressure to recover a second gaseous stream recover and a liquid stream rich in $C_5+$ hydrocarbons;

a distillation tower operatively connected for fractionating said second separator liquid stream to provide an overhead stream rich in $C_4-$ hydrocarbons and a bottom fractionator stream containing a major portion of $C_{10}+$ distillate boiling range hydrocarbons and a minor portion of $C_5-C_9$ gasoline boiling range hydrocarbons;

means for withdrawing an overglash stream rich in $C_5-C_9$ hydrocarbons from a mid-portion of said distillation tower;

fluid handling means for combining said overglash stream with a second portion of said first low-temperature separator liquid stream to provide a liquid recycle dilvent stream to the conversion zoned.

7. The system of claim 6 including means for maintaining said liquid q weight ratio of first low-temperature separator liquid stream to said overflash stream of between 4:1 and 2:1.

8. The system of claim 6 wherein said catalyst comprises an acid metallosilicate zeolite catalyst having a constraint index of about 1 to 12 at a reaction temperature of about 230° to 325° at process pressure of about 4,000 to 7,000 kPa to convert a major amount of feedstock olefins.

9. The system of claim 6 including means for maintaining said first separator temperature at about 38° C. and pressure of about 4,300 kPa; and means for maintaining said second separator temperature at about 42° C. at a pressure of about 1,330 kPa.

* * * * *

UNITED STATES PATENT AND TRADEMARK OFFICE
CERTIFICATE OF CORRECTION

PATENT NO. : 5,059,744

DATED : October 22, 1991

INVENTOR(S) : Harandi et al.

It is certified that error appears in the above-identified patent and that said Letters Patent is hereby corrected as shown below:

Column 8, line 44, "reacotor" should read --reactor--
Column 8, line 61, "constraing" should read --constraint--
Column 10, line 17, "overglash" should read --overflash--
Column 10, line 20, "overglash" should read --overflash--
Column 10, line 23, "dilvent" should read --diluent--
Column 10, line 23, "zoned" should read --zone--

Signed and Sealed this

Twenty-fourth Day of August, 1993

Attest:

BRUCE LEHMAN

*Attesting Officer*  *Commissioner of Patents and Trademarks*